US006407131B1

(12) United States Patent
Quada, Jr. et al.

(10) Patent No.: US 6,407,131 B1
(45) Date of Patent: Jun. 18, 2002

(54) COMPOUNDS AND METHOD FOR USE THEREOF IN THE TREATMENT OF CANCER OR VIRAL INFECTIONS

(75) Inventors: James C. Quada, Jr.; Joseph K. Agyin, both of San Antonio, TX (US); James Berger Camden, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/676,030

(22) Filed: Sep. 29, 2000

Related U.S. Application Data

(63) Continuation-in-part of application No. 08/857,811, filed on May 16, 1997.

(51) Int. Cl.[7] ............................................. A61K 31/415

(52) U.S. Cl. ....................................................... 514/395

(58) Field of Search ........................................ 514/395

(56) References Cited

U.S. PATENT DOCUMENTS

| | | | |
|---|---|---|---|
| 3,010,968 A | 11/1961 | Loux ........................ | 260/309.2 |
| 3,370,957 A | 2/1968 | Wagner et al. ................. | 99/90 |
| 3,499,761 A | 3/1970 | Dersch | |
| 3,541,213 A | 11/1970 | Klopping .................... | 424/273 |
| 3,669,969 A | 6/1972 | Lunn ....................... | 260/256.4 |
| 3,738,995 A | 6/1973 | Adams et al. ............ | 260/309.2 |
| RE28,403 E | 4/1975 | Actor et al. | |
| 3,881,014 A | 4/1975 | Regel et al. ................ | 424/273 |
| 3,956,262 A | 5/1976 | Heyes et al. ................ | 260/140 |

(List continued on next page.)

FOREIGN PATENT DOCUMENTS

| | | |
|---|---|---|
| EP | 617968 | 10/1994 |
| FR | 2155888 | 5/1973 |
| GB | 1123317 | 8/1968 |
| JP | 07 277 956 | 10/1995 |
| WO | WO 96/32107 | 10/1976 |
| WO | WO 94/04541 | 3/1994 |
| WO | WO 96/32103 | 10/1996 |
| WO | WO 96/32104 | 10/1996 |
| WO | WO 96/32115 | 10/1996 |
| WO | WO 96/40119 | 12/1996 |
| WO | WO 96/40120 | 12/1996 |
| WO | WO 96/40122 | 12/1996 |
| WO | WO 97/05870 | 2/1997 |
| WO | WO 97/05872 | 2/1997 |
| WO | WO 97/05873 | 2/1997 |
| WO | WO 98/32440 | 7/1998 |
| WO | WO 98/51303 | 11/1998 |
| WO | WO 98/51304 | 11/1998 |
| WO | WO 99/59585 | 11/1999 |
| WO | WO 00/21504 | 4/2000 |
| WO | WO 00/50007 | 8/2000 |

OTHER PUBLICATIONS

Latif et al., Jpn. J. Med. Sci. Biol. (1993), 46(5–6), 203–14, (abstract only).*
Chemical Abstracts 65:6570h referring to BE patent, date unknown, published by The American Chemical Society.
Berg et al., "Synergistic effects of photoactivated tetra(4–sulfonatophenyl)porphine and nocodazole on microtubule assembly, accumulation of cells in mitosis and cell survival.", Journal of Photochemistry and Photobiology B: Biology, vol. 13, pp. 59–70, (1992), Elsevier Sequoia.
Berg et al., "Synergistic effects of photoactivated tetra(4–sulfonatophenyl)porphine and nocodazole on microtubule assembly, accumulation of cells in mitosis and cell survival.", Journal of Photochemistry and Photobiology B: Biology, vol. 13, pp. 59–70, (1992), Abstract 10 pages, Chemical Abstracts AN 1992–251202, (2001), American Chemical Society.
Delatour et al., Therapie, vol. 31, No. 4., pp. 505–515, (1976), and translation thereof.
Elgebaly et al., J. Natl. Cancer Inst.,vol. 74, No. 4, pp. 811–815 (1985).
Friedman, et al., Biochimica et Biophysica Acta, 544 (1978) pp. 605–614.
Lacey, et al., Biochemical Pharma, vol. 34, No. 19, pp. 3603–3605 (1985).
Chemical Abstracts 121:175012z, (1994) p 607, Katiyar, et. al.
Stedman's Medical Dictionary, 24th ed., 1983, pp. 777–778.
Aur, J. Pediatr., 78, No. 1, (1971) pp. 129–131.
Lundy et al., Cancer Treat. Rep., vol. 62, No. 11, (1978), pp. 1955–1962.
Lundy et al., Surg. Forum, vol. 27, No. 62 (1976) pp. 132–134.
Marinovich, et al., Toxicol., vol. 94, No. 1–3, (1994) pp 173–85.
Lovett, Diss. Abstr. Int., (Sci), vol. 39, No. 11, (1979) pp. 5315–5316.
Brabender, et al., Cancer Research, vol. 36 (Mar. 1976) pp. 905–916.
Atassi et al., Europ., J. Cancer, vol. 11 (1975) pp. 599–607.
Brown, et al., J. Am. Chem. Soc., 83:1764–65 (1961).
Grenda, et al., J. Org. Chem. 30,259 (1965).
W. T. Thompson, Agricultural Chemicals Book IV, Fungicides, pp. 154, 121, 123 (1993–1994).
Carter, W.A. CRC Press, Selective Inhibitors of Viral Functions, pp. 277–346 (1975).
Merck Index, Eighth Edition, 1968, p. 1035.

(List continued on next page.)

Primary Examiner—Dwayne C. Jones
Assistant Examiner—C. Delacroix-Muirheid
(74) Attorney, Agent, or Firm—Bart S. Hersko

(57) ABSTRACT

Benzimidazole derivatives and salts and prodrugs thereof are disclosed, together with methods for the treatment of cancers or viral infections in warm blooded animals by administration of these compounds. Such compounds may be used in combination with a chemotherapeutic agent and/or a potentiator.

20 Claims, No Drawings

U.S. PATENT DOCUMENTS

| | | | |
|---|---|---|---|
| 4,046,906 A | 9/1977 | Frensch et al. | 424/273 |
| 4,731,366 A | 3/1988 | Munro et al. | 514/278 |
| 4,814,329 A | 3/1989 | Harsanyi et al. | 514/396 |
| 5,098,923 A | 3/1992 | Karjalainen et al. | 514/396 |
| 5,114,951 A | 5/1992 | King | 514/290 |
| 5,149,527 A | 9/1992 | Weisenthal | |
| 5,284,662 A | 2/1994 | Koparkar et al. | |
| 5,290,801 A | 3/1994 | Higley et al. | 514/395 |
| 5,310,748 A | 5/1994 | Wilde et al. | 514/395 |
| 5,329,012 A | 7/1994 | Anderson | 548/318.5 |
| 5,364,875 A | 11/1994 | Wilde | 514/375 |
| 5,434,163 A | 7/1995 | Edlind et al. | 514/310 |
| 5,441,742 A | 8/1995 | Autant et al. | |
| 5,554,373 A | 9/1996 | Seabrook | |
| 5,629,341 A | 5/1997 | Camden | |
| 5,656,615 A | 8/1997 | Camden | |
| 5,665,713 A | 9/1997 | Camden | |
| 5,665,751 A | 9/1997 | Camden | |
| 5,767,138 A | 6/1998 | Camden | |
| 5,770,616 A | 6/1998 | Camden | |
| 5,840,742 A | 11/1998 | Camden | |
| 5,854,231 A | 12/1998 | Camden | |
| 5,872,142 A | 2/1999 | Camden | |
| 5,880,144 A | 3/1999 | Camden | |
| 5,900,429 A | 5/1999 | Camden | |
| 5,902,804 A | 5/1999 | Camden | |
| 5,908,855 A | 6/1999 | Camden | |
| 5,929,099 A | 7/1999 | Camden | |
| 5,932,604 A | 8/1999 | Camden | |
| 5,932,609 A | 8/1999 | Camden | |
| 6,025,377 A | 2/2000 | Camden | |
| 6,077,862 A | 6/2000 | Camden | |
| 6,090,796 A * | 7/2000 | Camden | 514/89 |
| 6,110,953 A * | 8/2000 | Camden | 514/383 |
| 6,136,835 A * | 10/2000 | Camden | 514/383 |
| 6,177,460 B1 * | 1/2001 | Camden | 514/485 |
| 6,200,922 B1 * | 3/2001 | Camden | 514/331 |
| 6,228,876 B1 * | 5/2001 | Camden | 514/383 |
| 6,245,789 B1 * | 6/2001 | Camden | 514/365 |
| 6,251,870 B1 * | 6/2001 | Camden | 514/43 |
| 6,262,093 B1 * | 7/2001 | Camden | 514/365 |
| 6,265,427 B1 * | 7/2001 | Camden | 514/388 |
| 6,271,217 B1 * | 8/2001 | Camden | 514/110 |

OTHER PUBLICATIONS

DuPont, Material Safety Data Sheet Benlate Fungicide, Sep. 27, 1994.
Derwent Publications, AN 95–400884 and Japan Patent Abstracts, JP 07 277956 (see above) (1995).
Teicher, et al., Breast Cancer Research and Treatment, vol. 36, No. 2, pp 227–236 (1995).
Bissery, et al., Seminars in Oncology: Management of Breast Cancer: A New Therapeutic Approach, vol. 22, No. 6–S13, pp. 3–16, (1995).
Chemical Abstracts 113:112365 (1990) Ghannoum, et al.
Ram, et al., J. Med. Chem., 35, No. 3, 539–547 (1992).
Nene, et al., International Science Publisher, Fungicides in Plant Disease Control, Chapter 9, 1993.
Private Communication to Dr. Von Hoff from National Institute of Health, National Cancer Society (1995).
Chemical Abstracts 92:123231 (1979) Menzel et al.
Lacey et al., International Journal for Parasitology, vol. 18 No. 7, pp 885–936 (1988).
Merck Index, $12^{th}$ ed., 7943 and 9877, Merck & Co. (NJ 1996).
Chemical Abstracts 102:217569 (1985) Elgebaly et al.
Chemical Abstracts 87:161659 (1997) Lundy et al.
Lacey, et al., Biochemical Pharma., vol. 34, No. 7, pp. 1073–1077 (1985).
Lassnau, et al., Chest, vol. 104, pp 119–122 (1993).
Georgopapadakov et al., Science vol. 264, pp. 371–373 (Apr. 15, 1994).
Carter et al., Chemotherapy of Cancer, $2^{nd}$ Ed., John Wiley & Sons, NY, NY (1981), pp. 362–365.
Lapras, M. et al. Bull. Soc. Sci. Vet. et Med. comparee, Lyon, 1975, vol. 77, No. 6, pp. 379–397 (in French,—and English translation thereof.
Chemical Abstracts 98:66765, Vergieva (1982).

* cited by examiner

COMPOUNDS AND METHOD FOR USE THEREOF IN THE TREATMENT OF CANCER OR VIRAL INFECTIONS

The present application is a continuation-in-part of co-pending U.S. application Ser. No. 08/857,811, filed May 16, 1997, the entire disclosure of which is incorporated by reference herein.

TECHNICAL FIELD

The present invention relates to benzimidazole derivatives and their use for the treatment of cancer or a viral infection in warm blooded animals, particularly in humans and other mammals. The methods may use such a compound in combination with a potentiator or a chemotherapeutic agent.

BACKGROUND OF THE INVENTION

Cancers are a leading cause of death in animals and humans. The exact cause of cancer is not known, but links between certain activities such as smoking or exposure to carcinogens and the incidence of certain types of cancers and tumors has been shown by a number of researchers.

Many types of chemotherapeutic agents have been shown to be effective against cancers and tumor cells, but not all types of cancers and tumors respond to these agents. Unfortunately, many of these agents also destroy normal cells. The exact mechanism for the action of these chemotherapeutic agents are not always known.

Despite advances in the field of cancer treatment the leading therapies to date are surgery, radiation and chemotherapy. Chemotherapeutic approaches are said to fight cancers that are metastasized or ones that are particularly aggressive. Such cytocidal or cytostatic agents work best on cancers with large growth factors, i.e., ones whose cells are rapidly dividing. To date, hormones, in particular estrogen, progesterone and testosterone, and some antibiotics produced by a variety of microbes, alkylating agents, and anti-metabolites form the bulk of therapies available to oncologists. Ideally cytotoxic agents that have specificity for cancer and tumor cells while not affecting normal cells would be extremely desirable. Unfortunately, none have been found and instead agents that target especially rapidly dividing cells (both tumor and normal) have been used.

Clearly, the development of materials that would target cancer cells due to some unique specificity for them would be a breakthrough. Alternatively, materials that were cytotoxic to cancer cells while exerting mild effects on normal cells would be desirable.

Human Immunodeficiency Virus (HIV), the etiological agent for AIDS (acquired immune deficiency syndrome), is a member of the lentiviruses, a subfamily of retroviruses. HIV integrates its genetic information into the genome of the host. Most importantly, HIV infects and invades cells of the immune system; it breaks down the body's immune system and renders the patient susceptible to opportunistic infections and neoplasms. HIV-1 is cytopathic for T4 lymphocytes, cells of the immune system that express the cell surface differentiation antigen CD4. In addition to CD4+T cells, the host range of HIV includes cells of the mononuclear phagocytic lineage, including blood monocytes, tissue macrophages, Langerhans cells of the skin and dendritic reticulum cells within lymph nodes.

Precursor cells in the bone marrow are released into the blood in an immature circulating form known as monocytes. Monocytes use the blood strictly as a transport medium. Once they arrive where they're going to be used, they leave the blood and complete differentiation into macrophages. Cells of the monocyte/macrophage lineage are a major target population for infection with HIV in the body and are thought to provide reservoirs of virus for disseminating infection throughout the body. HIV is also neurotropic, capable of infecting monocytes and macrophages in the central nervous system causing severe neurologic damage. They can interact and fuse with CD4-bearing T cells, causing T cell depletion and thus contributing to the pathogenesis of AIDS.

Progression from HIV infection to AIDS is primarily determined by the effects of HIV on the cells that it infects, including CD4+T lymphocytes and macrophages. In turn, cell activation, differentiation and proliferation regulate HIV infection and replication in those cells. HIV and other lentiviruses can proliferate in nonproliferating, terminally differentiated macrophages and growth-arrested T lymphocytes. This ability of lentiviruses, including HIV, to replicate in nonproliferating cells, particularly in macrophages, is believed to be unique among retroviruses.

Due to the above-mentioned problems in the art, the present inventors have sought improvements and provide such improvements herein.

Carbendazim or 2-methoxycarbonylaminobenzimidazole has been studied as a cancer treatment. See U.S. Pat. No. 5,767,138 issued Jun. 16, 1998 to J. B. Camden. Carbendazim metabolizes in the body through the hydroxylation of the benzene ring, primarily in the 5-position. The metabolite is not as active in the treatment of cancer as the 2-methoxycarbonylaminobenzimidazole. Moreover, the benzimidazoles are not easily soluble in water. The derivatives described herein are more soluble and still maintain cytoxicity comparable to carbendazim.

SUMMARY OF THE INVENTION

The compounds of the present invention are represented by the following formula A:

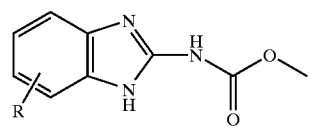

wherein
R is —COOR$_1$, —CONR$_1$R$_2$, —OCOR$_1$ or —NHCOR$_1$;
R$_1$ is alkyl, haloalkyl, hydroxyalkyl, alkenyl, haloalkenyl, cycloalkyl, cycloalkalkyl, heterocycloalkyl, heterocycloalkalkyl, substituted or unsubstituted phenyl, substituted or unsubstituted phenylamino, substituted or unsubstituted benzyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl; and
R$_2$ is hydrogen or alkyl.

The phenyl group, the phenylamino group, or the benzyl group may optionally be substituted with one or more nitro, carboxy, hydroxy, alkyl, alkoxy, or halide substituents.

Pharmaceutically acceptable salts of the benzimidazole derivatives of formula A are also included in the present invention. Further included in the invention are the prodrugs of the compounds of formula A.

In one embodiment of the invention, the benzimidazole derivatives of the invention are of the formula A-1:

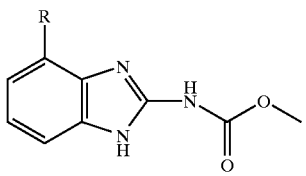

and preferably the compounds are of formula A-1 where R is —OCOR$_1$, more preferably where R$_1$ is substituted or unsubstituted phenyl.

In another embodiment of the invention, the benzimidazole derivatives are of the formula A-2:

In another embodiment of the invention, the benzimidazole derivatives are of the formula A-3:

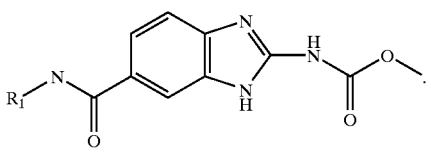

In another embodiment of the invention, the benzimidazole derivatives are of the formula A-4:

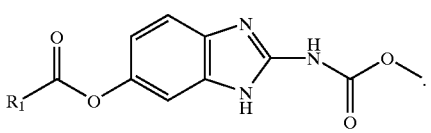

In another embodiment of the invention, the benzimidazole derivatives are of the formula A-5:

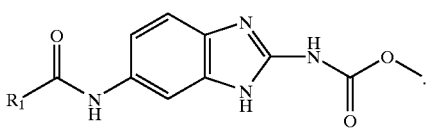

Methods are provided by the present invention for treatment of warm blooded animals, and in particular, humans and other mammals, that are affected by cancer or viral infection, the methods comprising administering a therapeutically effective amount of a benzimidazole derivative of formula A, or a salt or a prodrug thereof, to the animal.

DETAILED DESCRIPTION OF THE INVENTION

A. Definitions

The term "alkyl" refers to a fully strated monovalent hydrocarbon radical of 1 to 12 carbon atoms. It may be straight-chain or branched. Preferred are those alkyl groups containing 1 to 10 carbon atoms, with 2 to 8 carbon atoms particularly preferred.

The term "alkenyl" refers to an unsaturated monovalent hydrocarbon radical of 2 to 12 carbon atoms containing only carbon and hydrogen and having one or more double bonds. It may be straight-chain or branched. Preferred are those alkenyl groups containing 2 to 10 carbon atoms, with 2 to 8 carbon atoms particularly preferred.

The term "alkoxy" means the group —OR' wherein R' is alkyl. Preferred are alkoxy groups having 1 to 10 carbon atoms, more preferably 2 to 8 carbon atoms.

The term "alkoxyalkyl" refers to an alkoxy group covalently attached to an alkyl group. The alkoxy group contains from 1 to 12, preferably from 1 to 6 carbon atoms. The alkoxy group may be substituted with one or more hydroxyl groups (an "hydroxyalkoxyalkyl") or with one or more halogen atoms (a "haloalkoxyalkyl"); preferably the hydroxyl or halogen is on the terminal end of the alkoxyalkyl substituent The term "poly(alkoxy)alkyl" denotes 2 to 200, preferably 2 to 20, alkoxy groups covalently linked in either a linear or a branched configuration and attached to an alkyl group. Linear poly(alkoxy)alkyl moieties have a structure such as —(CH$_2$)$_m$—O—(CH$_2$)$_m$—O—(CH$_2$)$_m$—(CH$_2$)$_m$— . . . —O—C$_m$H$_{2m+1}$, where "m" is an integer, the same or different along the length of the chain. Branched moieties have two or more (—O—(CH$_t$)$_m$—) groups bound to a common third (—O—(CH$_t$)$_m$—) group, where "t" has a value that is independently selected from 0, 1 and 2 for each (CH$_t$)$_m$ group. Linear configurations are preferred. The number of repeating (—O—(CH$_t$)$_m$) groups within a substituent may be up to 200, preferably from 2 to 20, more preferably from 2 to 7, and most preferably is 2–5. The individual alkoxy groups may be the same or different, and individual alkoxy groups preferably contain from 1 to 6 carbon atoms each, and most preferably from 1 to 3 carbon atoms each. A presently preferred poly(alkoxy)alkyl is —(CH$_2$)$_y$—(OCH$_2$CH$_2$)$_x$—OCH$_3$ or —(CH$_2$)$_y$—OCH$_2$CH$_2$)$_x$—OCH$_2$CH$_3$, where y=1–4 and x=1–100, preferably 1–10, and more preferably, 2–5. The individual alkoxy groups may be substituted with one or more hydroxyl groups (an "hydroxypoly (alkoxy)alkyl") or with one or more halogen atoms (a "halopoly(alkoxy)alkyl"); preferably the hydroxyl or halogen is on the terminal end of the poly(alkoxy)alkyl substituent.

"Heterocyclo" designates a heterocyclic group; that is, a closed-ring structure, usually of either 5 or 6 members, in which one or more of the atoms in the ring is an element other than carbon, such as for example sulfur, nitrogen, or oxygen. A heterocyclic group may be, but is not limited to, pyridine, pyrrole, furan, thiophene, morpholine, and purine, optionally substituted with one or more nitro, carboxy, sulfonic acid, hydroxy, alkyl, alkoxy, or halide substituents.

The term "amino" refers to primary amines (—NH$_2$), secondary amines (—NHR'), and tertiary amines (—NR'R"), where R' and R" are the same or different substituent groups, such as alkyl, alkenyl, halogen, hydroxy, and the like.

"Independently" signifies that two or more of the groups immediately preceding the term are either identical or different; i.e., selection of one from the list following the term does not affect selection of the other(s).

"Substituted" encompasses both single and multiple substitutions, the latter including multiple substitutions by the same substituent as well as mixtures of different substituents.

The term "optional" or "optionally" means that the subsequently described event or circumstance may or may not occur, and that the description includes instances in which said event or circumstance occurs and instances in which it does not. For example, "optionally substituted phenyl" means that the phenyl may or may not be substituted and that the description includes both unsubstituted phenyl and phenyl wherein there is substitution. As another example, "optionally" followed by "converting the free base to the acid addition salt" means that such conversion may or may not be carried out in order for the process described to fall within the invention, and the invention includes those processes wherein the free base is converted to the acid addition salt and those processes in which it is not.

As used herein, "a therapeutically effective amount" means the concentration or quantity or level of the compound of the present invention that can attain a particular medical end, such as control or destruction of cancer cells, virally-infected cells, or viruses without producing unacceptable toxic symptoms. The term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the type of mammal being treated, the duration of the treatment, the nature of concurrent therapy (if any), and the specific formulations employed and the structure of the compounds or its salts.

As used herein, a "pharmaceutical addition salt" or "pharmaceutically acceptable salt" is a salt of the benzimidazole derivative compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and others known to those of ordinary skill in the art.

As used herein, the term "prodrug" refers to a form of a benzimidazole derivative compound that has minimal therapeutic activity until it is converted to its desired biologically active form. A prodrug is a compound having one or more functional groups or carriers covalently bound thereto, which functional groups or carriers are removed from the compound by metabolic processes within the body to form the respective bioactive compound.

As used herein, the term "metabolite" refers to the breakdown or end product of a benzimidazole derivative compound or its salt produced by metabolism or biotransformation in the animal or human body; e.g., biotransformation to a more polar molecule such as by oxidation, reduction, or hydrolysis, or to a conjugate (see Goodman and Gilman, "The Pharmacological Basis of Therapeutics" $8^{th}$ Ed., Pergamon Press, Gilman et al. (eds), 1990 for a discussion of biotransformation). As used herein, the metabolite of a benzimidazole derivative compound or its salt may be the biologically active form of the compound in the body. An assay for activity of a metabolite of a benzimidazole derivative of the present invention is known to one of skill in the art in light of the present disclosure, for example, testing for efficacy against a virus in vitro or in vivo.

As used herein, a "subject in need thereof" is a warm blooded animal having cancer or having a viral infection.

As used herein, "cancer" refers to all types of cancers, or neoplasms or benign or malignant tumors. In one embodiment, those cancers that attack normal healthy blood cells or bone marrow are contemplated by the present invention. Preferred cancers for treatment using methods provided herein include carcinoma, sarcoma, lymphoma, or leukemia. By "carcinoma" is meant a benign or malignant epithelial tumor and includes, but is not limited to, breast carcinoma, prostate carcinoma, non-small cell lung carcinoma, colon carcinoma, CNS carcinoma, melanoma carcinoma, ovarian carcinoma, or renal carcinoma. A preferred host is a human host.

A "viral infection" as used herein means an infection due to a DNA virus or an RNA virus (retrovirus). Examples of a double-stranded DNA virus are the Herpes virus and the influenza virus. Human immunodeficiency virus (HIV) is a prototype for retroviruses, i.e., viruses that use reverse transcription to replicate. However, certain DNA viruses use, in part, reverse transcription mechanisms to replicate such as, for example, the Hepatitus B virus. "Viruses" include retroviruses such as HIV or HTLV, influenza, rhinoviruses, herpes, hepatitis, or the like.

As used herein, a benzimidazole derivative of formulas A and A-1 through A-5, or a pharmaceutical salt thereof or a prodrug thereof, are "compounds of the present invention." Such compounds are further set forth under B infra.

As used herein, "chemotherapeutic agents" includes DNA-interactive agents, antimetabolites, tubulin-interactive agents, hormonal agents and others, such as asparaginase or hydroxyurca, and are as further set forth under D infra.

As used herein, "potentiators" are materials that affect the immune system or enhance the effectiveness of a compound of the present invention and are further set forth under E herein.

Following long-standing patent law convention, the terms "a" and "an" mean "one or more" when used in this application, including the claims.

B. Benzimidazole Derivatives

The benzimidazole derivatives of the present invention are those of formula A, as set forth above. Presently preferred compounds are those of formulas A-1 through A-5.

Pharmaceutically acceptable salts of the benzimidazole compounds are considered within the scope of compounds of the present invention. They are salts with an organic or inorganic acid. Preferred acid addition salts are chlorides, bromides, sulfates, nitrates, phosphates, sulfonates, formates, tartrates, maleates, malates, citrates, benzoates, salicylates, ascorbates, or the like. Such salts may be synthesized from the compound of the present invention, or derivative thereof, that contains a basic or acidic moiety, by conventional chemical methods. Generally, such salts may be prepared by reacting a free acid or base form of the compound, or derivative thereof, with a stoichiometric amount of the appropriate base or acid in water or in an organic solvent, or in a mixture of the two. Generally, nonaqueous media like ether, ethyl acetate, ethanol, isopropanol, or acetonitrile are preferred. Further suitable salts may be found in *Remington: The Science and Practice of Pharmacy*, 19th ed., Mack Publishing Company, Easton, Pa., 1995, p. 1457.

Pharmaceutically acceptable salts of the compounds of the present invention include conventional non-toxic salts or the quaternary ammonium salts of the compounds or derivatives formed, for example, from non-toxic inorganic or organic acids. For example, such conventional non-toxic salts include those derived from inorganic acids such as hydrochloric, hydrobromic, sulfuric, sulfamic, phosphoric, nitric, or the like; and salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, or the like. Preferred acid addition salts are chlorides, bromides, sulfates, nitrates, phosphates, sulfonates, formates, tartrates, maleates, malates, citrates, benzoates, salicylates, ascorbates, or the like. A presently preferred salt is the hydrochloride salt.

Further included within the scope of the compound, or salts thereof, useful for the present invention are prodrugs thereof. As used herein, a "prodrug" is a drug covalently bonded to a carrier wherein release of the drug occurs in vivo when the prodrug is administered to a mammalian subject. Prodrugs of the compounds of the present invention are prepared by modifying functional groups present in the compounds in such a way that the modifications are cleaved, either in routine manipulation or in vivo, to yield the desired compound. Prodrugs include compounds wherein hydroxy, amine, or sulfhydryl groups are bonded to any group that, when administered to a mammalian subject, is cleaved to form a free hydroxyl, amino, or sulfhydryl group, respectively. Examples of prodrugs include, but are not limited to, acetate, formate, or benzoate derivatives of alcohol or amine functional groups in the compounds of the present invention; phosphate esters, dimethylglycine esters, aminoalkylbenzyl esters, aminoalkyl esters or carboxyalkyl esters of alcohol or phenol functional groups in the compounds of the present invention; or the like.

Synthetic Reaction Parameters

The terms "solvent", "inert organic solvent" and "inert solvent" mean a solvent that is passive or non-reactive under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine, and the like). Unless specified to the contrary, the solvents used in the reactions of the present invention are inert organic solvents.

The reaction temperature can vary widely depending on the reactivity of the reactants. However, the temperature should not be so high as to decompose the reactants or so low as to cause inhibition of the condensation or freezing of the solvent. Unless specified to the contrary, the reactions described herein take place at atmospheric pressure over a temperature range from the temperature of dry ice to about 100° C., more preferably from about 10° C. to about 50° C., and most preferably at "room" or "ambient" temperature ("RT"), e.g. about 20° C.

Unless otherwise specified, the reaction times and conditions are intended to be approximate.

The time required for the reactions herein will depend to a large extent on the temperature being used and the relative reactivities of the starting materials. Therefore, the reaction time can vary greatly, for example from about five minutes to about two days. Various known techniques such as different types of chromatography, especially thin layer chromatography ("TLC"), gas chromatography ("GC"), or optical spectroscopy can be used to follow the progress of the reaction by the disappearance of the starting compound (s).

Isolation and purification of the compounds and intermediates described herein can be effected, if desired, by any suitable separation or purification procedure such as, for example, filtration, extraction, crystallization, column chromatography, thin-layer chromatography, thick-layer chromatography, centrifugal chromatography, or preparatory HPLC, or a combination of these procedures. Specific illustrations of suitable separation and isolation procedures can be found by reference to the examples hereinbelow. However, other equivalent separation or isolation procedures can, of course, also be used.

Synthesis of Compounds of Formula A

The compounds of the invention are prepared by modification to the benzimidazole carbamate nucleus:

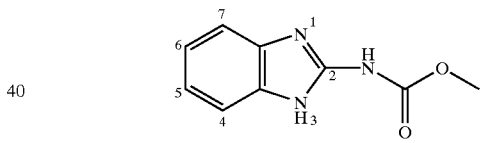

In one synthetic process, the known 5(6) carboxylic acid benzimidazole carbamate (101) is treated with thionyl chloride in benzene to activate the carboxyl group, then is derivatized with alcohols or amines to form compounds of formula A-2 (102) or A-3 (103) (Reaction Scheme 1), following procedures known to those of skill in the art.

Reaction Scheme 1

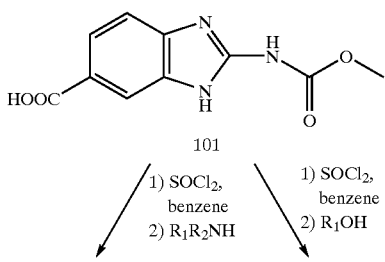

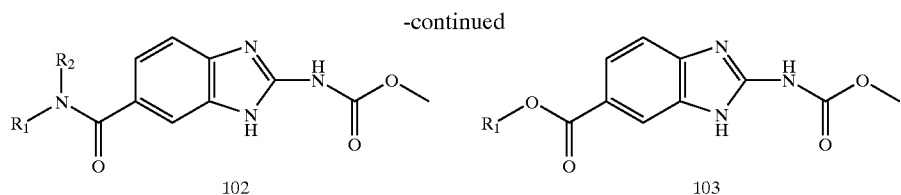

Similarly, to prepare compounds of Formula A-1 where R is —COOR$_1$ or —CONR$_1$R$_2$, the 4(7) carboxylic acid benzimidazole carbamate is treated with thionyl chloride in benzene to activate the carboxyl group, then is derivatized with alcohols or amines following the procedures of Reaction Scheme 1 to form the compounds of formula A-1 where R is —COOR$_1$ or —CONR$_1$R$_2$.

To prepare compounds of Formula A-5, the known 5(6)-amino benzimidazole carbamate (201) is reacted with a carbonyl chloride (202) to give the 5(6)-carboxamide benzimidazole derivatives of formula A-5 (203) (Reaction Scheme 2), following procedures known to those of skill in the art.

Reaction Scheme 2

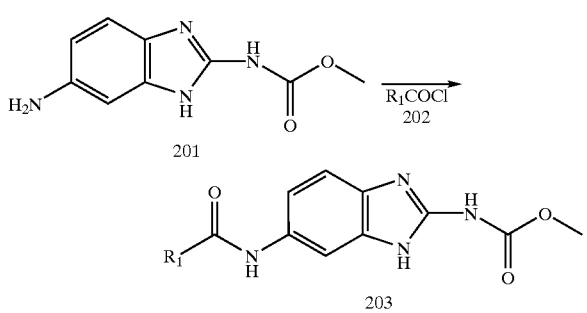

In a similar manner, to prepare compounds of Formula A-1 or A-4, the known 4(7) or 5(6) hydroxylated benzimidazole carbamate (301 or 302, respectively) is reacted with a carbonyl chloride (303) to give the 4(7) or the 5(6) carboxy benzimidazole derivatives of formula A-2 (304 or formula A-4 (305), respectively (Reaction Scheme 3), following procedures known to those of skill in the art.

Reaction Scheme 3

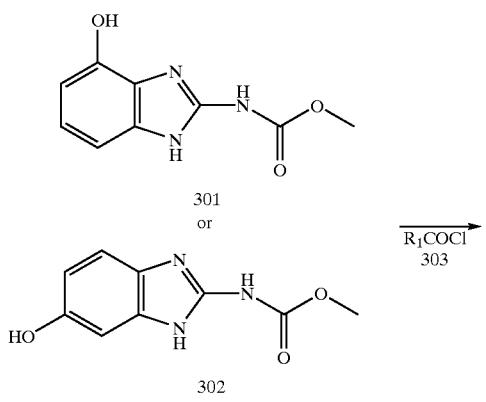

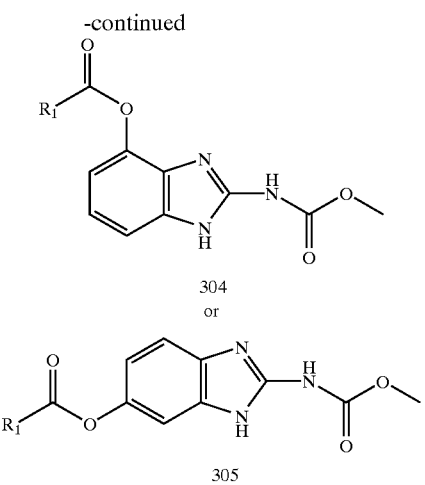

Presently Preferred Embodiments

In one embodiment of the present invention, presently preferred benzimidazole derivatives are those of Formula A-1 where R is selected from those groups listed in Table 1.

Solubility is based on a standard measure used in medicinal chemistry, the octanol-water partition coefficient, LogP, Lower Log) values indicate higher aqueous solubility. There are a variety of methods to estimate this value for a proposed structure using computer calculations. The below LogP solubility values were determined using the atom typing method of Ghose, Pritchett et al. (*J. Coinput Chem* 9(1): 80–90, 1988). Carbendazim has a LogP of 1.302.

TABLE 1

| Cpd. No. | R | Log P |
|---|---|---|
| 1-1 | —OCOCH$_2$CH(CH$_3$)CH$_2$C(CH$_3$)$_3$ | 3.712 |
| 1-2 | —OCOPh(3-OCH$_3$-4-OCH$_3$-5-OCH$_3$) | 1.955 |
| 1-3 | —COOCH$_2$CH=CH$_2$ | — |
| 1-4 | —COOCH$_2$CCl$_3$ | — |
| 1-5 | —CONHCH$_2$CH=CH$_2$ | — |
| 1-6 | —CONHCH$_2$CCl$_3$ | — |

In another embodiment of the invention, presently preferred benzimidazole derivatives are those of Formula A-2 where R$_1$ and R$_2$ are selected from those groups listed in Table 2:

TABLE 2

| Cpd. No. | R$_1$ | R$_2$ | LogP |
|---|---|---|---|
| 2-1 | —CH$_2$CH$_2$CH$_2$N(CH$_2$CH$_3$)$_2$ | H | 1.098 |
| 2-2 | —CH$_2$CH$_2$-morpholino | H | 0.018 |
| 2-3 | —CH(CH$_3$)CH$_2$CH$_3$ | H | 1.606 |

TABLE 2-continued

| Cpd. No. | $R_1$ | $R_2$ | LogP |
|---|---|---|---|
| 2-4 | —CH$_2$-(2-tetrahydrofuryl) | H | 0.613 |
| 2-5 | —CH$_2$CH$_2$CH(CH$_3$)$_2$ | H | 1.920 |
| 2-6 | —CH(CH$_3$)CH$_2$CH(CH$_3$)$_2$ | H | 2.333 |
| 2-7 | —CH$_2$CH$_2$C(CH$_3$)$_3$ | H | 2.353 |
| 2-8 | —CH$_2$CH(CH$_3$)CH$_2$CH$_3$ | H | 1.992 |
| 2-9 | —CH (CH$_2$CH$_3$)$_2$ | H | 2.075 |
| 2-10 | —CH$_2$CH$_2$CH$_2$N(CH$_3$)$_2$ | H | 0.413 |
| 2-11 | —CH$_2$CH$_2$OCH$_3$ | H | 0.217 |
| 2-12 | —NH—Ph | H | 1.737 |
| 2-13 | —Ph(2—OH) | H | 1.779 |
| 2-14 | —CH$_2$CH$_2$N(CH$_3$)$_2$ | H | 0.361 |
| 2-15 | —Ph(3-OCH$_3$-4-OCH$_3$-5-OCH$_3$) | H | 1.305 |
| 2-16 | cyclohexyl | CH$_3$ | 2.213 |
| 2-17 | —CH$_2$CH$_2$CH$_2$CH$_3$ | CH$_3$ | 1.836 |
| 2-18 | —CH$_2$CH$_2$CH$_3$ | CH$_2$CH$_2$CH$_3$ | 2.250 |

In another embodiment of the present invention, presently preferred benzimidazole derivatives are those of Formula A-3 where $R_1$ is selected from those groups listed in Table 3:

TABLE 3

| Cpd. No. | $R_1$ | Log P |
|---|---|---|
| 3-1 | —CH$_2$CH$_2$CH$_2$CH$_2$Cl | 2.239 |
| 3-2 | —CH$_2$CH$_2$OCH$_2$CH$_2$Cl | 1.571 |
| 3-3 | —CH$_2$CH═CH$_2$ | 1.772 |
| 3-4 | —(CH$_2$CH$_2$O)$_2$CH$_2$CH$_3$ | 1.045 |
| 3-5 | —CH$_2$CH$_2$OCH$_2$CH$_2$OH | 0.424 |
| 3-6 | —CH$_2$CH$_2$CH═CH$_2$ | 2.024 |
| 3-7 | —CH$_2$Ph | 2.808 |
| 3-8 | —CH$_2$CH$_2$N(CH$_3$)$_2$ | 1.011 |
| 3-9 | —CH$_2$CH$_2$CH$_2$Cl | 1.788 |
| 3-10 | —CH$_2$CH═CHCH$_2$OH | 1.121 |
| 3-11 | —CH$_2$CH$_2$CH$_2$CH$_2$CH$_2$OH | 1.488 |
| 3-12 | —CH(CH$_2$Cl)$_2$ | 2.510 |
| 3-13 | —CH$_2$CH(CH$_3$)CH$_2$C(CH$_3$)$_3$ | 3.802 |
| 3-14 | —CH$_2$CF$_2$CF$_3$ | 2.841 |
| 3-15 | —CH(CH$_2$F)$_2$ | 1.423 |
| 3-16 | —CH(CH$_3$)(cyclopropyl) | 2.155 |
| 3-17 | —CH$_2$CH$_2$F | 0.542 |
| 3-18 | —CH(CH$_2$Br)$_2$ | 2.636 |
| 3-19 | —CH$_2$CH(CH$_3$)CH$_2$CH$_3$ | 2.256 |
| 3-20 | —CH$_2$CH$_2$CH(CH$_3$)CH$_2$C(CH$_3$)$_3$ | 4.126 |
| 3-21 | —CH$_2$CH$_2$CH(CH$_3$)CH$_2$CH$_2$CH═C(CH$_3$)$_2$ | 4.048 |

In a further embodiment, a preferred compound of the invention is of Formula A-4 where $R_1$ is —Ph(3-OCH$_3$-4-OCH$_3$-5-OCH$_3$)(Cpd. No. 4-1; LogP=1.955).

In yet another embodiment, a preferred compound is of Formula A-5 where $R_1$ is —CH$_2$CH(CH$_3$)CH$_2$C(CH$_3$)$_3$ (Cpd. No. 5-1; LogP=3.062).

C. Screening Assays

Screening assays for determining those cancers susceptible to treatment using compounds of the present invention include incubating cell line models representing specific cancers as set forth, for example, by the National Cancer Institute, in the presence and absence of such compounds. Viability of cells may be determined by the MTT assay (Promega Corp., Madison, Wis. 53711), or the SRB (sulforhodamine B) assay (Skehan, et al., *JNCI*, 82:13,1107, 1990). Susceptibility to said compounds exists when viability in the presence of a compound of the present invention is less than viability in the absence of such compound.

Exemplary cell line models representing specific cancers include, but are not limited to, the following:

Non-small cell lung cancer: NCIH23, NCIH324, NCIH522, A549/ATCC, A549(ASC), CALU1, EKVX, NCIH125M, NCIH226, NCIH520, SKMES1, NCIH322M, NCIH358M, NCIH460, NCIH292, HOP62, HOP18, HOP19, HOP92, LXFL 529, SW1573, LXFS 650L, ML1019, ML1076, ML1045, or UABLG22;

Small cell lung cancer: NCIH69, NCIH146, NCIH82, NCIH524, DMS 114, DMS 273, HOP27, SHP77, or RHOS;

Colon cancer: HT29, HCC2998, HCT116, LOVO, SW1116, SW620, COLO 205, DLD1, WIDR, COLO 320DM, HCT15, CXF 280, KM12, KM20L2, COLO 741, CXF 264L, COLO 746, UABC02, MLI059, CAC02, HT29/PAR, HT29/MDR1, or NB4;

Breast cancer: MCF7, MCF7/ADRRES, ZR751, ZR7530, MDAMB231/ATCC, HS 578T, UISOBCA1, MCF7/ATCC, SKBR3, MDAMB435, MDAN, BT549, T47D, MDAMB231, MAXF 401, BT474, or MDAMB468;

Ovarian cancer: OVCAR3, OVCAR4, OVCAR5, OVCAR8, A2780, IGROV1, SKOV3, OVXF 899, A1336, or ES2;

Leukemia: P388, P3888/ADR, CCRFCEM, CCRFSB, K562, MOLT4, L1210, HL60(TB), RPMI8226, SR, or K562/ADR;

Fibroblast: IMR90, or CCD19LU;

Renal cancer: UO31, SN12C, SN12S1, SN12K1, SN12L1, SN12A1, A498, A704, CAKI1, RXF 393, RXF631, 7860, SW156, TK164, 769P, SS78, ACHN, TK10, RXF 486L, UOK57, or UOK57LN;

Melanoma: LOX IMVI, MALME3M, RPM17951, SKMEL2, SKMEL5, SKMEL28, SKMEL31, UCSD 242L, UCSD 354L, M14, M19MEL, UACC62, UACC257, MEXF 514L, or UABMEL3;

Prostate cancer: PC3, PC3M, DU145, LNCAP, 1013L, UMSCP1, WIS, JE, RER, MRM, DHM, AG, RB, RVP, FC, WAE, DB/SMC, JCA1, ND1, WMF, TSUPRI, JECA, GDP, T10, WBW, RVP1, or WLL;

CNS cancer: SNB7, SNB19, SNB44, SNB56, SNB75, SNB78, U251, TE671, SF268, SF295, SF539, XF 498, SW 1088, SW 1783, U87 MG, SF767, SF763, A172, or SMSKCNY;

Bone/muscle: A204/ATCC, OHS, TE85, A673, CHA59, MHM 25, RH18, RH30, or RD; and

Lymphoma: AS283, HT, KD488, PA682, SUDHL7, RL, DB, SUDHL1, SUDHL4, SUDHL10, NUDUL1, or HUT 102.

D. Chemotherapeutic Agents

Chemotherapeutic agents are generally grouped as DNA-interactive agents, antimetabolites, tubulin-interactive agents, hormonal agents, other agents such as asparaginase or hydroxyurea, and agents as set forth in Table 3. Each of the groups of chemotherapeutic agents can be further divided by type of activity or compound. Chemotherapeutic agents used in combination with a compound of the present invention or salts thereof may be selected from any of these groups but are not limited thereto. For a detailed discussion of the chemotherapeutic agents and their method of administration, see Dorr, et al, Cancer Chemotherapy Handbook, 2d edition, pages 15–34, Appleton & Lange (Connecticut, 1994) herein incorporated by reference.

DNA-interactive agents include alkylating agents, e.g., cisplatin, cyclophosphamide, and altretamine; DNA strandbreakage agents, such as bleomycin; intercalating topoisomerase II inhibitors, e.g., dactinomycin and doxorubicin; nonintercalating topoisomerase II inhibitors, such as etoposide and teniposide; and the DNA minor groove binder plicamycin, for example.

The alkylating agents form covalent chemical adducts with cellular DNA, RNA, or protein molecules, or with smaller amino acids, glutathione, or similar chemicals. Generally, alkylating agents react with a nucleophilic atom in a cellular constituent, such as an amino, carboxyl, phosphate, or sulfhydryl group in nucleic acids, proteins, amino acids, or in glutathione. The mechanism and the role of these alkylating agents in cancer therapy is not well understood.

Typical alkylating agents include, but are not limited to, nitrogen mustards, such as chlorambucil, cyclophosphamide, isofamide, mechlorethamine, melphalan, uracil mustard; aziridine such as thiotepa; methanesulphonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine.

DNA strand breaking agents include bleomycin, for example.

DNA topoisomerase II inhibitors include the following intercalators, such as amsacrine, dactinomycin, daunorubicin, doxorubicin (adriamycin), idarubicin, and mitoxantrone; nonintercalators, such as etoposide and teniposide, for example.

A DNA minor groove binder is plicamycin, for example.

Antimetabolites interfere with the production of nucleic acids by one of two major mechanisms. Certain drugs inhibit production of deoxyribonucleoside triphosphates that are the immediate precursors for DNA synthesis, thus inhibiting DNA replication. Certain of the compounds are analogues of purines or pyrimidines and are incorporated in anabolic nucleotide pathways. These analogues are then substituted into DNA or RNA instead of their normal counterparts.

Antimetabolites useful herein include, but are not limited to, folate antagonists such as methotrexate and trimetrexate; pyrimidine antagonists, such as fluorouracil, fluorodeoxyuridine, CB3717, azacitidine, cytarabine, and floxuridine; purine antagonists include mercaptopurine, 6-thioguanine, fludarabine, pentostatin and ribonucleotide reductase inhibitors include hydroxyurea.

Tubulin interactive agents act by binding to specific sites on tubulin, a protein that polymerizes to form cellular microtubules. Microtubules are critical cell structure units. When the interactive agents bind the protein, the cell can not form microtubules Tubulin interactive agents include vincristine and vinblastine, both alkaloids and paclitaxel, for example.

Hormnonal agents are also useful in the treatment of cancers and tumors. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Further agents include the following: hydroxyurea appears to act primarily through inhibition of the enzyme ribonucleotide reductase, and asparaginase is an enzyme which converts asparagine to nonfunctional aspartic acid and thus blocks protein synthesis in the tumor.

Taxol (paclitaxel) is a preferred chemotherapeutic agent.

A listing of currently available chemotherapeutic agents according to class, and including diseases for which the agents are indicated, is provided as Table 3A.

TABLE 3A

Neoplastic Diseases[1] for which Exemplary Chemotherapeutic agents are Indicated

| Class | Type of Agent | Name | Disease[2] |
|---|---|---|---|
| Alkylating Agents | Nitrogen Mustards | Mechlorethamine ($HN_2$) | Hodgkin's disease, non-Hodgkin's lymphomas |
|  |  | Cyclophosphamide | Acute and chronic lymphocytic leukemias, Hodgkin's disease, |
|  |  | Ifosfamide | non-Hodgkin's lymphomas, multiple myeloma, neuroblastoma, breast, ovary, lung, Wilms' tumor, cervix, testis, soft-tissue sarcomas |
|  |  | Melphalan | Multiple myeloma, breast, ovary |
|  |  | Chlorambucil | Chronic lymphocytic leukemia, primary macroglobulinemia, Hodgkin's disease, non-Hodgkin's lymphomas |
|  |  | Estramustine | Prostate |
|  | Ethylenimines and Methyl-melamines | Hexamethylmelamine | Ovary |
|  |  | Thiotepa | Bladder, breast, ovary |
|  | Alkyl Sulfonates | Busulfan | Chronic granulocytic leukemia |
|  | Nitrosoureas | Carmustine | Hodgkin's disease, non-Hodgkin's lymphomas, primary brain tumors, multiple myeloma, malignant melanoma |
|  |  | Lomustine | Hodgkin's disease, non-Hodgkin's lymphomas, primary brain tumors, small-cell lung |
|  |  | Semustine | Primary brain tumors, stomach, colon |
|  |  | Streptozocin | Malignant pancreatic insulinoma, malignant carcinoid |
|  | Triazenes | Dacarbazine | Malignant melanoma, Hodgkin's disease, soft-tissue sarcomas |
|  |  | Procarbazine |  |
|  |  | Aziridine |  |

TABLE 3A-continued

Neoplastic Diseases[1] for which Exemplary Chemotherapeutic agents are Indicated

| Class | Type of Agent | Name | Disease[2] |
|---|---|---|---|
| Antimetabolites | Folic Acid Analogs | Methotrexate Trimetraxate | Acute lymphocytic leukemia, choriocarcinoma, mycosis fungoides, breast, head and neck, lung, osteogenic sarcoma |
| | Pyrimidine Analogs | Fluorouracil Floxuridine | Breast, colon, stomach, pancreas, ovary, head and neck, urinary bladder, premalignant skin lesions (topical) |
| | | Cytarabine Azacitidine | Acute granulocytic and acute lymphocytic leukemias |
| | Purine Analogs and Related Inhibitors | Mercaptopurine | Acute lymphocytic, acute granulocytic, and chronic granulocytic leukemias |
| | | Thioguanine | Acute granulocytic, acute lymphocytic, and chronic granulocytic leukemias |
| | | Pentostatin | Hairy cell leukemia, mycosis fungoides, chronic lymphocytic leukemia |
| | | Fludarabine | Chronic lymphocytic leukemia, Hodgkin's and non-Hodgkin's lymphomas, mycosis fungoides |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | | Vindesine | Vinca-resistant acute lymphocytic leukemia, chronic myelocytic leukemia, melanoma, lymphomas, breast |
| | Epipodophyllotoxins | Etoposide Teniposide | Testis, small-cell lung and other lung, breast, Hodgkin's disease, non-Hodgkin's lymphomas, acute granulocytic leukemia, Kaposi's sarcoma |
| | Antibiotics | Dactinomycin | Choriocarcinoma, Wilms' tumor, rhabdomyosarcoma, testis, Kaposi's sarcoma |
| | | Daunorubicin | Acute granulocytic and acute lymphocytic leukemias |
| | | Doxorubicin 4'-Deoxydoxorubicin | Soft-tissue, osteogenic, and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung, and genitourinary tract; Hodgkin's disease, non-Hodgkin's lymphomas |
| | | Plicamycin | Testis, malignant hypercalcemia |
| | | Mitomycin | Stomach, cervix, colon, breast, pancreas, bladder, head and neck |
| | Enzymes | L-Asparaginase | Acute lymphocytic leukemia |
| | Taxanes | Docetaxel | Breast, ovarian |
| | Taxoids | Paclitaxel | |
| | Biological Response Modifiers | Interferon Alfa | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| | | Tumor Necrosis Factor | Investigational |
| | | Tumor-Infiltrating Lymphocytes | Investigational |
| Miscellaneous Agents | Platinum Coordination Complexes | Cisplatin Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essential thrombocytosis, malignant melanoma |
| | Methyl Hydrazine Derivative | Procarbazine | Hodgkin's disease |
| | Adrenocortical Suppressant | Mitotane | Adrenal cortex |
| | | Aminoglutethimide | Breast |
| Hormones and Antagonists | Adrenocorti-costeroids | Prednisone | Acute and chronic lymphocytic leukemias, non-Hodgkin's lymphomas, Hodgkin's disease, breast |
| | Progestins | Hydroxy-progesterone caproate | Endometrium, breast |
| | | Medroxy-progesterone acetate | |
| | | Megestrol acetate | |
| | Estrogens | Diethylstil-bestrol Ethinyl estradiol | Breast, prostate |
| | Antiestrogen | Tamoxifen | Breast |
| | Androgens | Testosterone propionate Fluoxy-mesterone | Breast |
| | Antiandrogen | Flutamide | Prostate |
| | Gonadotropin-releasing hormone analog | Leuprolide Goserelin | Prostate, Estrogen-receptor-positive breast |

[1]Adapted from Calabresi, P., and B. A. Chabner, "Chemotherapy of Neoplastic Diseases" Section XII, pp 1202–1263 in: Goodman and Gilman's The Pharmacological Basis of Therapeutics, Eighth ed., 1990 Pergamin Press, Inc.;
and Barrows, L. R. "Antineoplastic and Immunoactive Drugs", Chapter 75, pp 1236–1262, in: Remington: The Science and Practice of Pharmacy, Mack Publishing Co. Easton, PA, 1995.;
both references are incorporated by reference herein, in particular for treatment protocols.
[2]Neoplasms are carcinomas unless otherwise indicated.

E. Potentiators

A "potentiator," as used herein, is a material that improves or increases the efficacy of the benzimidazole derivatives or a salt or a prodrug thereof, or that acts on the immune system as an immunomodulator. Potentiators can be used in combination with a compound of the present invention. A potentiator may be an antiviral agent. One such potentiator is triprolidine or its cis-isomer. Triprolidine is described in U.S. Pat. No. 5,114,951 (1992, the patent is incorporated by reference herein). A further potentiator is procodazole, (also named 1H-benzimidazole-2-propanoic acid, or β-(2-benzimidazole) propionic acid or 2-(2-carboxyethyl) benzimidazole or propazol). Procodazole is a non-specific immunoprotective agent active against viral and bacterial infections and may be used in combination with the compounds set forth herein. Procodazole is effective with a compound of the present invention, alone in treating cancers, tumors, leukemia or viral infections, or combined with a chemotherapeutic agent.

Further potentiators include, but are not limited to, propionic acid, salts thereof, or esters thereof; antioxidant vitamins such as vitamins A, C, E, or beta-carotene; abacavir; AL-721 (lipid mixture); amprenavir; Amphotericin B methyl ester; Ampligen (mismatched RNA); anti-AIDS antibody; anti-human interferon-α-antibody; anti-AIDS antibody, ascorbic acid and derivatives thereof; AS-101 (heavy metal based immunostimulant); azidothymidine; β-interferon; Bropirimine; butylated hydroxytoluene; Ciamexon, Cimetidine; CL-246,738, colony stimulating factors, including GM-CSF; Creme Pharmatex (benzalkonium chloride); CS-82 (5-unsubstituted derivative of Zidovudine); Cyclosporin; D-penicillamine (3-mercapto-D-valine); delavirdine; dextran sulphate; dinitrochlorobenzene; efavirenz; erythropoietin; Foscarnet (trisodium phosphonoformate); fusidic acid; ganciclovir; glucan; glycyrrhizin, HPA-23 (ammonium-21-tungsto-9-antimonate); human immunevirus antiviral; hyperimmune gamma-globulin, IMREG-1, IMREG-2; indinavir; interferon-cc; interferon-gamma; interleukin-1 or interleukin-2; isoprinosine; Krestin; LC-9018; lamivudine; lentilart; LF-1695; methionine-enkephalin; Minophagen C; muramyl tripeptide; naltrexone; nelfinavir; Neutropin; nevirapine; Nonoxinol; Ornidyl (eflomithine); non-nucleoside inhibitors of reverse transcriptase; nucleoside analogues (ddA, ddC, ddI, ddT, ddG, AZT, and the like); pentamidine isethionate; Phenytoin; polymannoacetate; Peptide T (octapeptide sequence); protease inhibitors; Ribavirin; Rifabutin (ansamycin); ritonavir; RNA immunomodulator; rsT4 (recombinant soluble T4); saquinavir; shosaikoto and ginseng; SK-818 (germanium-derived antiviral); sodium diethylthiocarbarmate; stavudine; stearic acid derivative; suramin and analogues thereof; thymic humoral factor; TP-5; Thymosin fraction 5 and Thymosin 1; Thymostimulin; TNF (tumor necrosis factor), vitamin B preparations; Trimetrexate; UA001; -interferon or acyclovir, for example.

A compound, or a salt or a prodrug thereof, of the present invention may be combined with a potentiator and with a chemotherapeutic agent in the methods of the present invention.

F. Dosage

Any suitable dosage may be administered in the methods of the present invention. The compound or salt or prodrug thereof chosen for a particular application, the carrier and the amount will vary widely depending on the species of the warm blooded animal or human, the type of cancer, or the particular viral infection being treated, and depending upon the effective inhibitory concentrations observed in trial studies. The dosage administered will, of course, vary depending upon known factors, such as the pharmacodynamic characteristics of the particular compound, salt, or combination and its mode and route of administration; the age, health, or weight of the subject; the nature and extent of symptoms; the metabolic characteristics of the drug and patient, the kind of concurrent treatment; the frequency of treatment; or the effect desired.

Generally a dosage of as little as about 1–2 milligram (mg) per kilogram (kg) of body weight is suitable, but preferably as little as 10 mg/kg and up to about 10,000 mg/kg may be used. Preferably, a dosage from 15 mg/kg to about 5000 mg/kg is used. Most preferably, the dose is between 150 mg/kg to about 1000 mg/kg. Doses useful in the treatment of cancer or viral infections are 250 mg/kg, 500 mg/kg, 800 mg/kg, 1000 mg/kg, 1500 mg/kg, 2500 mg/kg, 3500 mg/kg, 4000 mg/kg, 5000 mg/kg, or 6000 mg/kg. Any range of doses can be used. Generally, a compound, salt thereof, prodrug thereof, or combination of the present invention can be administered on a daily basis one or more times a day, or one to four times a week, either in a single dose or separate doses during the day. Twice-weekly dosing over a period of at least several weeks is preferred, and often dosing will be continued over extended periods of time and possibly for the lifetime of the patient. However, the dosage and the dosage regimen will vary depending on the ability of the patient to sustain the desired and effective plasma levels of the compounds of the present invention, or salt or prodrug thereof, in the blood.

The compound, salt thereof, prodrug thereof, or combination may be micronized or powdered so that it is more easily dispersed and solubilized by the body. Processes for grinding or pulverizing drugs are well known in the art. For example, a hammer mill or similar milling device can be used. The preferred particle size is less than about $100\mu$ and preferably less than $50\mu$.

Intravenously, the most preferred doses may range from about 1 to about 10 mg/kg/minute during a constant rate infusion.

The dosage for humans is generally less than that used in mice and is typically about 1/12 of the dose that is effective in mice. Thus, if 500 mg/kg was effective in mice, a dose of 42 mg/kg would be used in humans. For a 60 kg man, this dose would be 2520 mg.

The compounds and salts and prodrugs thereof of the present invention are generally safe. The $LD_{50}$ is high, about 1500 mg/kg given orally in mice and there are no special handling requirements. The compounds can be given orally, and since they are not very soluble, they are preferably given in tablet form or as a suspension. Alternatively, when micronized to sufficiently small size, they may be and preferably are given as an injection.

The compounds and salts and prodrugs thereof of the present invention may be administered in a unit dosage form which may be prepared by any methods known to one of skill in the art in light of the present disclosure. Unit dosages may include from 1 milligram to 1000 milligrams of active ingredient. Preferably the dosage unit will contain from about 10 mg to about 500 mg active ingredient. The active ingredient is generally present in an amount of about 0.5% to about 95% by weight based on the total weight of the dosage unit.

For intravenous use, preferred dosages may range from about 1 to about 10 mg/kg/minute during a constant rate infusion.

A dosage unit may comprise a single compound, or mixtures thereof, with other compounds or other cancer- or viral-inhibiting compounds. The dosage unit may comprise diluents, extenders, carriers, liposomes, or the like. The unit may be in solid or gel form such as pills, tablets, capsules and the like or in liquid form suitable for oral, rectal, topical, intravenous injection or parenteral administration or injection into or around the treatment site. The range and ratio of benzimidazole derivative, or salt or prodrug thereof, to chemotherapeutic agent or to potentiator will depend on the type of cancer or viral infection being treated and the particular chemotherapeutic agent or potentiator.

G. Formulations

Formulations of the present invention include the compound of the present invention, a salt thereof or a prodrug thereof and, optionally, a chemotherapeutic agent and, optionally, a poteritiator generally mixed with a pharmaceutically acceptable carrier. A "pharmaceutical carrier" is a pharmaceutically acceptable solvent, suspending agent or vehicle for delivering a compound of the present invention to the animal or human. The carrier may be liquid or solid and is selected with the planned manner of administration in mind. A "pharmaceutically acceptable" component is one that is suitable for use with humans and/or animals without undue adverse side effects (such as toxicity, irritation, and allergic response) commensurate with a reasonable benefit/risk ratio.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary, or paste.

Generally, formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" in the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also preferred carriers.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin, cyclodextrin derivatives, or the like.

Capsule or tablets can be easily formulated and can be made easy to swallow or chew. Tablets may contain suitable carriers, binders, lubricants, diluents, disintegrating agents, coloring agents, flavoring agents, flow-inducing agents, or melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethylcellulose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, or the like. Lubricants used in these dosage forms include sodium oleate, sodium stearate, magnesium stearate, sodium benzoate, sodium acetate, sodium chloride, or the like. Disintegrators include, for example, starch, methyl cellulose, agar, bentonite, xanthan gum, or the like. Molded tablets may be made by molding in a suitable machine a mixture of the powdered active ingredient moistened with an inert liquid diluent.

The tablets may optionally be coated or scored and may be formulated so as to provide slow- or controlled-release of the active ingredient. Tablets may also optionally be provided with an enteric coating to provide release in parts of the gut other than the stomach.

Exemplary pharmaceutically acceptable carriers and excipients that may be used to formulate oral dosage forms of the present invention are described in U.S. Pat. No. 3,903,297 to Robert, issued Sep. 2, 1975, incorporated by reference herein. Techniques and compositions for making dosage forms useful in the present invention are described in the following references: 7 Modem Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound that enhances absorption or penetration of the active ingredient through the skin or other affected areas. Examples of such dermal penetration enhancers include dimethylsulfoxide and related analogues.

The oil phase of an emulsion used to treat subjects in the present invention may be constituted from ingredients known to one of skill in the art in light of the present disclosure. An emulsion may comprise one or more emulsifiers. For example, an oily phase may comprise at least one emulsifier with a fat or an oil, with both a fat and an oil, or a hydrophilic emulsifier may be included together with a lipophilic emulsifier that acts as a stabilizer. Together, the emulsifier(s), with or without stabilizer(s), make up an emulsifying wax, and the wax together with the oil and/or fat make up the emulsifying ointment base that forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono-or dibasic alkyl esters, mineral oil. The choice of suitable oils or fats for the formulation is based on achieving the desired cosmetic properties, the properties required and compatibility with the active ingredient.

Compounds of the present invention may also be administered vaginally, for example, as pessaries, tampons, creams, gels, pastes, foams or spray formulations containing appropriate carriers in addition to the active ingredient. Such carriers are known in the art in light of the present disclosure.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous formulations isotonic with the blood of the intended recipient; and aqueous and non-aqueous sterile suspensions which may include suspending systems designed to target the compound to blood components or one or more organs. The formulations may be presented in unit-dose or multi-dose sealed containers, for example, ampoules or vials. Extemporaneous injections solutions and suspensions may be prepared from sterile powders, granules and tablets of the kind previously described. Parenteral and intravenous forms may also include minerals and other materials to make them compatible with the type of injection or delivery system chosen.

In general, water, a suitable oil, saline, aqueous dextrose (glucose), or related sugar solutions and glycols such as propylene glycol or polyethylene glycols are suitable carriers for parenteral solutions. Solutions for parenteral administration preferably contain a water soluble salt of the active ingredient, suitable stabilizing agents and, if necessary, buffer substances. Antioxidizing agents, such as sodium bisulfite, sodium sulfite, or ascorbic acid, either alone or combined, are suitable stabilizing agents. Also used are citric acid salts thereof, or sodium EDTA. In addition, parenteral solutions may contain preservatives, such as benzalkonium chloride, methyl- or propyl-paraben, or chlorobutanol. Suitable pharmaceutical carriers are described in Remington, cited supra.

The present invention additionally contemplates administering compounds of the herein described invention for use in the form of veterinary formulations, which may be prepared, for example, by methods that are conventional in the art in light of the present disclosure.

Useful pharmaceutical dosage formulations for administration of the compounds of the present invention are illustrated as follows:

Capsules: A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules: A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets: A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable: A parenteral composition suitable for administration by injection is prepared by stirring 1.5% by weight of active ingredient in 10% by volume propylene glycol and water. The solution is made isotonic with sodium chloride and sterilized.

Suspension: An aqueous suspension is prepared for oral administration so that each 5 ml contains 100 mg of finely divided active ingredient, 200 mg of sodium carboxymethyl cellulose, 5 mg of sodium benzoate, 1.0 g of sorbitol solution, U.S.P., and 0.025 ml of vanillin.

Compounds of the present invention may be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

H. Method Of Treatment

The method of treatment can be any suitable method which is effective in the treatment of the particular cancer or viral infection that is being treated. Treatment includes administering a therapeutically effective amount of the compounds of the present invention in a form described hereinabove, to a subject in need of treatment.

Compounds of the present invention can be administered by any means that produces contact of the active agent with the agent's site of action in the body, for example, suitable means including, but not limited to, oral, rectal, nasal, topical (including transdermal, aerosol, buccal or sublingual), vaginal, parenteral (including subcutaneous, intramuscular, intravenous or intradermal), intravesical, or injection into or around the cancer or site of viral infection. They can be administered by any conventional means available for use in conjunction with pharmaceuticals, either as individual therapeutic agents or in a combination of therapeutics. Preferably, compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder, or in a liquid form, or as a liposome.

The preferred route will vary with the condition and age of the recipient, virus or cancer being treated nature of the disorder, or severity of disorder. It is believed that oral administration, or parenteral treatment is the preferred method of administering the compounds to subjects in need thereof.

In each of the above-described methods, the administering may be in vivo, or may be ex vivo. In vivo treatment is useful for treating diseases in a mammal, preferably the mammal is a human; and ex vivo treatment is useful for purging body fluids, such as blood, plasma, bone marrow, and the like, for return to the body. The nation's blood supply is currently tested for antibodies to HIV. However, the test is still imperfect and samples that yield negative tests can still contain HIV virus. Treating blood and blood products with the compounds of the present invention can add an extra margin of safety to kill any retrovirus that may have gone undetected. Body tissue may be internal or external to an animal body, or, for example, may be the surface skin of the animal.

I. Combination Therapy

Compounds of the present invention may additionally be combined with chemotherapeutic agents and/or potentiators to provide a combination therapy. Combination therapy is intended to include any chemically compatible combination of a compound of the present invention with other compounds of the present invention or other compounds outside of the present invention, as long as the combination does not eliminate the activity of the compound of the present invention. For example, one or more compounds may be combined with a potentiator or with a chemotherapeutic agent. In the case of retroviral infection, a combination therapy with nucleoside analogues such as AZT, nonnucleoside reverse transcriptase inhibitors, TC-3, or protease inhibitors is contemplated by the present invention. In the case of hepatitis, acyclovir, famciclovir or valacyclovir, Ribavirin, interferon, or combinations of Ribavirin and interferon or beta globulin is contemplated as a combination therapy. For herpes, a recombinant alpha interferon can be used as a combination therapy. The active agent can be coadministered, for example, in the form of a tablet or capsule, liposome, as an agglomerated powder, or in a liquid form. The amount of chemotherapeutic agent or potentiator used can be lower than that of the benzimidazole derivative. It will be present in a dosage unit in an amount that provides an operative combination with the benzimidazole derivative. The dosage of the chemotherapeutic agent or the potentiator can range from about 0.5 mg/kg body weight to about 400 mg/kg body weight.

Combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example, treatment with one agent on day 1 and the other on day 2. The exact regimen will depend on the disorder being treated, the severity of the disorder, and the response to the treatment.

In addition to the use of chemotherapeutic agents and potentiators, a benzimidazole derivate or a salt or a prodrug thereof can be combined with a fungicide or an herbicide. Preferred herbicides and fungicides include carbendazim, fluoconazole, benomyl, glyphosate, and propicodazole.

J. Pharmaceutical Kits

The present invention also includes pharmaceutical kits useful, for example, for the treatment of cancer or viral infection. The kits comprise one or more containers containing a pharmaceutical composition comprising a therapeutically effective amount of a compound of the present invention or a salt or a prodrug thereof. Such kits can further include, if desired, one or more of various conventional pharmaceutical kit components, such as, for example, containers with one or more pharmaceutically acceptable carriers, additional containers, etc., as will be readily apparent to those skilled in the art. Instruction, such as e.g. printed instructions either as inserts or as labels or the like, the instruction indicating quantities of the components to be administered, guidelines for administration, and/or guidelines for mixing the components, can also be included with the kit.

K. Studies

The following studies were performed to test the effectiveness of the benzimidazole derivatives of the present invention against certain cancers and viral infections.

Colon and Melanoma Tumor Cells Test:

The following cell culture tests were performed to test the toxicity of benzimidazole derivative compounds of the present invention on colon and melanoma tumor cells. The viability of the cells were tested by looking at MTT (3-[4, 5-dimethylthiazol-2-yl]-2,5-diphenyltetrazolium bromide) reduction. MTT assay is a well known measure of cell viability.

The colon tumor cells (HT29) and the melanoma cells (B16 murine melanoma) were seeded (1000–2000 cells) into each well of a 96-well microtiter plate and allowed to grow. Twenty-four hours later, increasing concentrations of each benzimidazole derivative were added to the plates and the cells were allowed to incubate for 3–6 days in the presence of the drugs. MTT reagent was then added to the wells and allowed to incubate for 4 hours at 37° C., after which the formazan metabolite was solubilized with acidic isopropanol and the absorbance was read. Experimental controls included blank wells to which no cells were added (zero point of formazan absorbance) and control wells to which no drug was added (highest level of formazan absorbance). Each drug concentration was tested in duplicate and the resulting average absorbance was plotted against drug concentration using the EZ-ED50 computer program on a personal computer interfaced to the microtiter plate reader.

The program fit the resulting curves to a four-parameter equation:

$$Y = \frac{A_{max} - A_{min}}{\left(1 + \frac{X}{IC50}\right)^n} + A_{min}$$

where $A_{max}$ and $A_{min}$ are, respectively, the absorbances in the absence and presence of highest drug concentration, X is the drug concentration and Y is the absorbance at that concentration, n is the slope of the curve, and $IC_{50}$. is the concentration of drug that gives 50% growth inhibition. The $IC_{50}$ value is then derived from this equation by EZ-ED50. The $IC_{50}$ values for growth inhibition of both B16 and HT29 cancer cell lines are reported in Table 4 below (Y=H unless otherwise indicated).

TABLE 4

| Cpd. No. | $IC_{50}$ ($\mu$M) | |
|---|---|---|
| | Murine Melanoma | Human Colon Carcinoma |
| 1-1 | 20.1 | 15.8 |
| 1-2 | 14.0 | 26.3 |
| 2-1 | 530.3 | 397.8 |
| 2-2 | 80.5 | 121.0 |
| 2-3 | 2.9 | 1.6 |
| 2-4 | 47.2 | 35.7 |
| 2-5 | 5.9 | 5.1 |
| 2-6 | 0.84 | 0.50 |
| 2-7 | 0.41 | 0.42 |
| 2-8 | 5.0 | 4.9 |
| 2-9 | 0.37 | 228.3 |
| 2-10 | 553.2 | 446.9 |
| 2-11 | 30.5 | 17.1 |
| 2-12 | 271.3 | 25.4 |
| 2-13 | 2.8 | 2.3 |
| 2-14 | 402.7 | 158.0 |
| 2-15 | 6.1 | 4.2 |
| 2-16 | 0.32 | 0.23 |
| 2-17 | 4.6 | 2.5 |
| 2-18 | 9.4 | 3.1 |
| 3-1 | 0.011 | 0.010 |
| 3-2 | 0.082 | 0.036 |
| 3-3 | 0.22 | 0.059 |
| 3-4 | 0.084 | 0.027 |
| 3-5 | 2.6 | — |
| 3-6 | 0.044 | 0.0076 |
| 3-7 | 0.085 | 0.033 |
| 3-8 | 70.4 | 48.6 |
| 3-9 | 0.21 | 0.054 |
| 3-10 | 1.0 | 0.60 |
| 3-11 | 248.1 | 107.4 |
| 3-12 | 0.99 | 2.1 |
| 3-13 | 0.0046 | 0.019 |
| 3-14 | 588.2 | 313.5 |
| 3-15 | 0.94 | 0.61 |
| 3-16 | 0.062 | 0.030 |
| 3-17 | 0.97 | 0.30 |
| 3-18 | 1.2 | 2.1 |
| 3-19 | 0.048 | 0.012 |
| 3-20 | <0.001 | 0.013 |
| 3-21 | 0.077 | 0.046 |
| 4-1 | 0.25 | 0.17 |
| 5-1 | 6.6 | 7.0 |

Microtubule Inhibition Assay:

The benzimidazole derivatives of this invention were evaluated for their ability to inhibit formation of microtubules, following the procedure of Luduena, R. F. and M. C. Roach (*Pharmacol. Ther.* 49: 133–152 (1991)). Tubulin was purified from bovine brain by a cycle of assembly and disassembly, followed by phosphocellulose chromatography and gel filtration (Fellous, A. et al., *Eur. J. Biochem.* 78(1): 167–174 (1977)). The assay was performed by preparing a sample of tubulin protein under conditions which promote polymerization into microtubules (Prasad, V. et al., *J. Protein Chem.* 11(5): 509–515 (1992)), then adding the benzamidazole derivatives, at 2 $\mu$M, and following the time course of polymerization. Microtubule polymerization was followed by performing the reaction in a cuvette and monitoring UV absorbance at 350 nm, allowing direct visualization of the time course of the polymerization. After 30 minutes, polymerization was complete and the percent inhibition of polymerization was calculated as the final absorbance of the reaction taken as a percentage of the final absorbance of a control polymerization reaction run in parallel without drug added. These data are reported in Table 5 below.

TABLE 5

| Tubulin Polymerization Inhibition | |
|---|---|
| Cpd. No. | % Inhibition |
| 1-1 | 38 |
| 1-2 | 35 |
| 2-1 | 24 |
| 2-2 | 11 |
| 2-3 | 26 |
| 2-4 | 36 |
| 2-5 | 37 |
| 2-6 | 12 |
| 2-7 | 43 |
| 2-8 | none |
| 2-9 | 16 |
| 2-10 | 5 |
| 2-11 | 19 |
| 2-12 | 50 |
| 2-13 | 27 |
| 2-14 | none |
| 2-15 | 5 |
| 2-16 | 39 |
| 2-17 | none |
| 2-18 | 42 |
| 3-1 | 28 |
| 3-2 | 14 |
| 3-3 | 42 |
| 3-4 | 12 |
| 3-5 | 10 |
| 3-6 | 12 |
| 3-7 | 26 |
| 3-8 | none |
| 3-9 | none |
| 3-10 | none |
| 3-11 | 50 |
| 3-12 | 11 |
| 3-13 | 28 |
| 3-14 | 23 |
| 3-15 | 45 |
| 3-16 | 44 |
| 3-17 | 8 |
| 3-18 | none |
| 3-19 | 28 |
| 3-20 | 35 |
| 3-21 | 2 |
| 4-1 | 2 |
| 5-1 | none |

DNA Binding Assay:

The DNA binding assay was performed in a manner very similar to that of the MTT cell growth inhibition assay above. The assay was based upon the ability of the test compounds to displace methyl green (Sigma) from DNA and the resultant hydration of the free methyl green molecule to a colorless derivative (Burres, N. S. et al., *J. Nat. Prod.* 55(11): 1582–1587 (1992); Kim and Nordén, *FEBS Lett.* 315(1): 61–64 (1993)). As for the MTT assay, each drug concentration was assayed in duplicate and the data were averaged before analysis. Experimental controls in this assay included wells containing free methyl green solution with no DNA, for fully decolorized background absorbance, and methyl green-DNA complex (Sigma) without drug, for the highest possible methyl green absorbance. Methyl green-DNA in buffer was added to each well to obtain $A_{655}$ of approximately 0.7. Serial dilutions of drug in buffer were added and the plates were mixed, then allowed to stand at room temperature for 24 hours to allow for displacement and hydration of the free methyl green. The absorbance at 655 nm was measured as a function of added drug concentration in an automated microplate reader, and the data were reduced by the computer program EZ-ED50 to derive $IC_{50}$ values (concentration at which 50% of the methyl green is displaced from DNA).

None of the benzimidazole derivatives listed in Table 4 or 5 showed any DNA interaction by this assay.

In vivo B16 Murine Melanoma Tumor Model

B6D2F1 mice received interperitoneally (i.p.) inocula of B16 murine melanoma brei prepared from B16 tumors growing s.c. in mice (Day 0). On Day 1, mice were randomized into groups, with 20 mice in the control group and 10 mice in each treated group (except there were 8 mice in selected groups given compound 3–13. Treatment with drugs or vehicle control was started on Day 1.

The mean survival times of all groups were calculated and results were expressed as mean survival of treated mice/mean survival of control mice (T/C)×100%. A "T/C" value of 150 means that the mice in the treated group lived 50% longer than those of the control group; this is sometimes referred to as the increase in life span, or ILS value.

Mice that survived for at least 60 days were considered to be long-term survivors, or cures, in the B16 model. The universally accepted cut-off for activity in this model, which has been used for years by the NCI, is T/C=125. Conventional use of B16 over the years has set the following levels of activity:

T/C<125, no activity
T/C=125–150, weak activity
T/C=150–200, modest activity
T/C=200–300, high activity
T/C>300, with long-term survivors=excellent, curative activity.

Three of the four analogs tested were generally inactive against the B16 murine melanoma model using the dosing regimen described above. Compound 3-1, at 50 mg/kg/i.p., showed weak activity using the NCI's criteria for defining antitumor activity. In addition, one long-term survivor was observed with this compound and dosing regimen. The results are presented in Table 6, below.

TABLE 6

Benzimidazole Derivatives vs. B16 Murine Melanoma

| Cpd. | # | Dose/Route[1] | Schedule | Weight Change (Day 12) | T/C (%) | # of Survivors | # of Toxic Deaths |
|---|---|---|---|---|---|---|---|
| Cntrl | 20 | Tween 80/i.p | qd × 5 | +6.9% | 100 | 0 | 0 |
| 3-1 | 10 | 100 mg/kg/i.p | qd × 5 | +12.9% | 108 | 0 | 0 |
| 3-1 | 10 | 50 mg/kg/i.p | qd × 5 | +7.5% | 132 | 1 | 0 |
| 3-1 | 10 | 20 mg/kg/i.v | qd × 5 | +6.3% | 98 | 0 | 0 |
| 3-1 | 10 | 10 mg/kg/i.v | qd × 5 | +9.3% | 97 | 0 | 0 |
| 3-6 | 10 | 100 mg/kg/i.p | qd × 5 | +8.9% | 118 | 0 | 0 |
| 3-6 | 10 | 50 mg/kg/i.p | qd × 5 | +9.4% | 119 | 0 | 0 |
| 3-6 | 10 | 20 mg/kg/i.v | qd × 5 | +6.5% | 99 | 0 | 0 |
| 3-6 | 10 | 10 mg/kg/i.v | qd × 5 | +8.7% | 107 | 0 | 0 |
| 3-13 | 10 | 100 mg/kg/i.p | qd × 5 | +9.8% | 75 | 0 | 0 |
| 3-13 | 10 | 50 mg/kg/i.p | qd × 5 | +12.5% | 94 | 0 | 0 |
| 3-13 | 8 | 5 mg/kg/i.v. | qd × 5 | +3.6% | 91 | 0 | 7 |
| 3-13 | 8 | 2.5 mg/kg/i.v | qd × 5 | +11.7% | 92 | 0 | 0 |
| 3-19 | 10 | 100 mg/kg/i.p | qd × 5 | +10.8% | 124 | 0 | 0 |
| 3-19 | 10 | 50 mg/kg/i.p | qd × 5 | +9.6% | 119 | 0 | 0 |
| 3-19 | 10 | 40 mg/kg/i.v | qd × 5 | +2.5% | 73 | 0 | 6 |
| 3-19 | 10 | 20 mg/kg/i.v | qd × 5 | +7.8% | 106 | 0 | 0 |

[1]i.p = interperitoneally
i.v = intravenously

EXAMPLES

Example 1

Synthesis of Cpd. No. 1-1

0.100 Grams (0.482 mmol) of methyl 2-amino-5-hydroxybenzimidazole carbamate and 0.171 g (0.966 mmol) of 3,5,5-trimethylhexanoyl chloride were mixed in 3 mL dry tetrahydrofuran under argon. The mixture was stirred at 23° C. for 16 hours and at 40° C. for 1 hour. The mixture was cooled to 23° C. and a precipitate was collected by filtration and recrystallized from ethyl acetate. The tan powder weighed 0.096 g (0.276 mmol, 57.2% yield).

Example 2

Synthesis of Cpd. No. 1-2

0.135 Grams (0.65 mmol) of methyl 2-amino-4-hydroxybenzimidazole carbamate and 0.150 g (0.65 mmol) of 3,4,5-trimethoxybenzoyl chloride were mixed in 2 mL dry tetrahydrofuran under argon. The mixture was stirred at 23° C. for 16 hours and at 40° C. for 1 hour. The mixture was cooled to 23° C. and a solid was collected by filtration and recrystallized from ethyl acetate. The gray powder weighed 0.128 g (0.318 mmol, 48.9% yield).

Example 3

Synthesis of methyl 5-chlorocarbonyl-1H-benzimidazole-2-carbamate 7.4 mL (12.069 g, 101.4 mmol) thionyl chloride and 1.80 g (7.66 mmol) methyl 5-carboxy-1H-benzimidazole-2-carbamate in 37 mL dry benzene were heated to reflux under argon for 3.5 hours. The mixture was then cooled to 23° C. and the solvent and excess thionyl chloride were distilled under reduced pressure. The resulting brown solid was stored under vacuum to remove all traces of thionyl chloride and used in the following Examples without further purification.

Example 4

Synthesis of Cpd. No. 2-14

0.150 Grams (0.591 mmol) of methyl 5-chlorocarbonyl-1H-benzimidazole-2-carbamate and 2.0 mL (1.606 g, 18.22 mmol) N,N-dimethylethylenediamine were stirred together in 3 mL dry tetrahydrofuran under argon for 16 hours at 23° C., then at 40° C. for one hour. The mixture was diluted with 5 mL dichloromethane, washed with saturated aqueous sodium carbonate, and the organic layer was dried over sodium sulfate, concentrated by evaporation under reduced pressure and cooled on an ice-water bath. The precipitated solid was collected by filtration and washed with ice-cold ethyl acetate to provide 0.018 g (0.059 mmol, 10.0% yield) of product as a tan powder.

Example 5

Synthesis of Cpd. No. 2-12

0.150 Grams (0.591 mmol) of methyl 5-chlorocarbonyl-1H-benzimidazole-2-carbamate and 2.0 mL (2.198 g, 20.33 mmol) phenylhydrazine were stirred together in 3 mL dry tetrahydrofuran under argon for 16 hours at 23° C., then at 40° C. for one hour. The mixture was diluted with 5 mL dichloromethane, washed with saturated aqueous sodium carbonate, and the organic layer was dried over sodium sulfate, concentrated by evaporation under reduced pressure and cooled on an ice-water bath. The precipitated solid was collected by filtration and washed with ice-cold ethyl acetate to provide 0.038 g (0.117 mmol, 19.8% yield) of product as a tan powder.

Example 6

Synthesis of Cpd. No. 2-6

To 0.203 g (0.800 mmol) of methyl 5-chlorocarbonyl-1H-benzimidazole-2-carbamate was added 2 mL dry tetrahydrofuran, followed by 1.0 mL (0.717g, 7.09 mmol) 1,3-dimethylbutylamine under argon. The mixture was stirred for 16 hours at 23° C., then the precipitated solid was collected by filtration, washed with diethyl ether, and recrystallized from methanol/diethyl ether to provide 0.157 g (0.493 mmol, 61.6% yield) of product as a white powder.

Example 7

Synthesis of Cpd. No. 2-16

To 0. 166 g (0.654 mmol) of methyl 5-chlorocarbonyl-1H-benzimidazole-2-carbamate was added 2 mL dry tetrahydrofuran, followed by 1.0 mL (0.868g, 7.668 mmol) N-methylcyclohexylamine under argon. The mixture was stirred for 16 hours at 23° C., then the precipitated solid was collected by filtration, washed with diethyl ether, and recrystallized from methanol/diethyl ether to provide 0.134 g (0.406 mmol, 62.1 % yield) of product as a tan powder.

Example 8

Synthesis of Cpd. No. 3-4

0.121 Grams (0.477 mmol) of methyl 5 -chlorocarbonyl-1H-benzimidazole-2-carbamate and 2.0 mL (1.998 g, 14.89 mmol) 2-(2-ethoxyethoxy)ethanol were stirred together under argon for 16 hours at 23° C., then at 40° C. for one hour. The mixture was diluted with 75 mL dichloromethane, washed with saturated aqueous sodium carbonate, and the organic layer was dried over sodium sulfate, concentrated by evaporation under reduced pressure and cooled on an ice-water bath. The precipitated solid was collected by filtration and washed with ice-cold ethyl acetate to provide 0.083 g (0.236 mmol, 49.5% yield) of product as an off-white powder.

Example 9

Synthesis of Cpd. No. 3-5

0.247 Grams (0.974 mmol) of methyl 5-chlorocarbonyl-1H-benzimidazole-2-carbamate and 2.0 mL (2.236 g, 21.07 mmol) diethylene glycol were stirred together under argon for 16 hours at 23° C., then at 40° C. for one hour. The mixture was diluted with 75 mL dichloromethane, washed with saturated aqueous sodium carbonate, and the organic layer was dried over sodium sulfate, concentrated by evaporation under reduced pressure and cooled on an ice-water bath. The precipitated solid was collected by filtration and washed with ice-cold ethyl acetate to provide 0.001 g (0.030 mmol, 3.1% yield) of product as a cream-colored powder.

Example 10

Synthesis of Cpd. No. 3-8

0.151 Grams (0.595 mmol) of methyl 5-chlorocarbonyl-1H-benzimidazole-2-carbamate and 2.0 mL (1.774 g, 19.90 mmol) N,N-dimethylethanolamine were stirred together under argon for 16 hours at 23° C., then at 40° C. for one hour. The mixture was diluted with 75 mL dichloromethane, washed with saturated aqueous sodium carbonate, and the organic layer was dried over sodium sulfate, concentrated by evaporation under reduced pressure and cooled on an ice-water bath. The precipitated solid was collected by filtration and washed with ice-cold ethyl acetate to provide 0.066 g (0.215 mmol, 36.1% yield) of product as a tan powder.

Example 11

Synthesis of Cpd. No. 3-12

0.100 Grams (0.394 mmol) of methyl 5-chlorocarbonyl-1H-benzimidazole-2-carbamate and 1.0 mL (1.351 g, 10.47 mmol) 1,3-dichloropropanol were stirred together under argon for 2.5 hours at 23° C., then at 40° C. for 16 hours. The mixture was diluted with 75 mL dichloromethane, washed with saturated aqueous sodium carbonate, and the organic layer was dried over sodium sulfate, concentrated by evaporation under reduced pressure and diluted with ice-cold diethyl ether. The precipitated solid was collected by filtration and dried under reduced pressure to provide 0.045 g (0.130 mmol, 33.0% yield) of product as an off-white powder.

Example 12

Synthesis of Cpd. No. 4-1

0.135 Grams (0.65 mmol)of methyl 2-amino-5-hydroxybenzimidazole carbamate and 0.150 g (0.65 mmol) of 3,4,5-trimethoxybenzoyl chloride were mixed in 2 mL dry tetrahydrofuran under argon. The mixture was stirred at 23° C. for 16 hours and at 40° C. for 1 hour. The mixture was cooled to 23° C. and a solid was collected by filtration and recrystallized from ethyl acetate. The tan powder weighed 0.080 g (0.199 mmol, 30.6% yield).

Example 13

Synthesis of Cpd. No. 5-1

To 0.171 g (0.966 mmol) of 3,5,5-trimethylhexanoyl chloride in 3 mL dry tetrahydrofuran under argon was added 0.074 g (0.359 mmol)of methyl 2-amino-(5-aminobenzimidazole) carbamate. The mixture was stirred at 23° C. for 16 hours and at 40° C. for 1 hour. The mixture was then cooled to 23° C. and a precipitate was collected by filtration and recrystallized from ethyl acetate. The white powder weighed 0.055 g (0.159 mmol, 44.3% yield).

What is claimed is:

1. A compound of the following formula A-4:

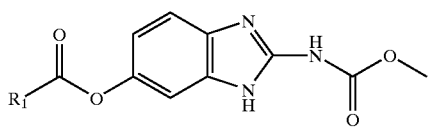

A-4 wherein,
$R_1$ is alkyl, haloalkyl, hydroxyalkyl, alkenyl, haloalkenyl, cycloalkyl, cycloalkalkyl, heterocycloalkyl, heterocycloalkalkyl, substituted phenyl wherein the substitution is alkoxy, unsubstituted phenyl, substituted or unsubstituted phenylamino, substituted or unsubstituted benzyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl.

2. A compound according to claim 1 wherein the compound is in the form of a pharmaceutically acceptable salt thereof.

3. A compound according to claim 2 wherein said pharmaceutically acceptable salt is a hydrochloride salt.

4. A compound according to claim 1 wherein the compound is in the form of a prodrug thereof.

5. A compound according to claim 1 wherein the compound is in the form of a liposome delivery system.

6. A compound according to claim 1 wherein $R_1$ is alkyl, substituted phenyl wherein the substitution is alkoxy, or unsubstituted phenyl.

7. The compound of claim 1 wherein $R_1$ is substituted phenyl wherein the substitution is trimethoxy.

8. A pharmaceutical composition comprising a compound of the following formula A-4:

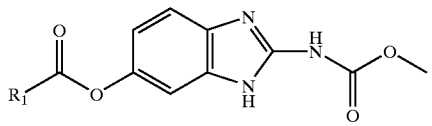

A-4 wherein,
$R_1$ is alkyl, haloalkyl, hydroxyalkyl, alkenyl, haloalkenyl, cycloalkyl, cycloalkalkyl, heterocycloalkyl, heterocycloalkalkyl, substituted phenyl wherein the substitution is alkoxy, unsubstituted phenyl, substituted or unsubstituted phenylamino, substituted or unsubstituted benzyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;
and, a pharmaceutically acceptable carrier.

9. A pharmaceutical composition according to claim 8 wherein the compound is in the form of a pharmaceutically acceptable salt thereof.

10. A pharmaceutical composition according to claims 9 wherein said pharmaceutically acceptable salt is selected from the group consisting of chloride, bromide, sulfate, nitrate, phosphate, sulfonate, formate, tartrate, maleate, malate, citrate, benzoate, salicylate, ascorbate, and mixtures thereof.

11. A pharmaceutical composition according to claim 9 wherein said pharmaceutically acceptable salt is a hydrochloride salt.

12. A pharmaceutical composition according to claim 8 wherein the compound is in the form of a prodrug thereof.

13. A pharmaceutical composition according to claim 8 wherein the pharmaceutically acceptable carrier is in the form of a liposome delivery system.

14. A pharmaceutical composition according to claim 8 wherein said compound is micronized and said composition is suitable for administration by injection.

15. A pharmaceutical composition according to claim 8 wherein said compound is coupled to a soluble polymer.

16. A pharmaceutical composition according to claim 8 wherein said compound is coupled to a biodegradable polymer.

17. A pharmaceutical composition according to claim 8 wherein $R_1$ is alkyl, substituted phenyl wherein the substitution is alkoxy, or unsubstituted phenyl.

18. A pharmaceutical composition according to claim 8 comprising from 1 mg to 1000 mg of said compound.

19. The pharmaceutical composition of claim 8 wherein $R_1$ is substituted phenyl wherein the substitution is trimethoxy.

20. A pharmaceutical kit comprising:
a therapeutically effective amount of a compound of the following formula A-4:

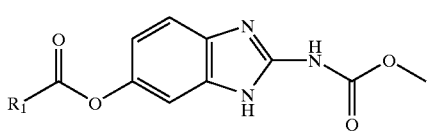

A-4 wherein,
$R_1$ is alkyl, haloalkyl, hydroxyalkyl, alkenyl, haloalkenyl, cycloalkyl, cycloalkalkyl, heterocycloalkyl, heterocycloalkalkyl, substituted phenyl wherein the substitution is alkoxy, unsubstituted phenyl, substituted or unsubstituted phenylamino, substituted or unsubstituted benzyl, alkoxyalkyl, poly(alkoxy)alkyl, hydroxyalkoxyalkyl, hydroxypoly(alkoxy)alkyl, haloalkoxyalkyl, halopoly(alkoxy)alkyl, or aminoalkyl;
and, instruction for use in treating cancer or a viral infection.

* * * * *

UNITED STATES PATENT AND TRADEMARK OFFICE
CERTIFICATE OF CORRECTION

PATENT NO.     : 6,407,131 B1
DATED          : June 18, 2002
INVENTOR(S)    : James C. Quada, Jr. et al.

It is certified that error appears in the above-identified patent and that said Letters Patent is hereby corrected as shown below:

<u>Title page,</u>
Item [54], Title, delete "METHOD" and replace with -- METHODS --.

<u>Column 32,</u>
Line 10, delete "claims" and replace with -- claim --.

Signed and Sealed this

Tenth Day of December, 2002

JAMES E. ROGAN
*Director of the United States Patent and Trademark Office*